US006461871B1

(12) United States Patent
Kubista et al.

(10) Patent No.: US 6,461,871 B1
(45) Date of Patent: Oct. 8, 2002

(54) METHOD FOR THE PREPARATION OF A PROBE FOR NUCLEIC ACID HYBRIDIZATION

(75) Inventors: Mikael Kubista, Mölnlycke; Nicke Svanvik, Göteborg; Gunnar Westman, Härryda, all of (SE)

(73) Assignee: Lightup Technologies AB, Huddinge (SE)

( * ) Notice: Subject to any disclaimer, the term of this patent is extended or adjusted under 35 U.S.C. 154(b) by 0 days.

(21) Appl. No.: 09/486,853

(22) PCT Filed: Sep. 4, 1998

(86) PCT No.: PCT/SE98/01580

§ 371 (c)(1),
(2), (4) Date: Apr. 5, 2000

(87) PCT Pub. No.: WO99/13105

PCT Pub. Date: Mar. 18, 1999

(30) Foreign Application Priority Data

May 9, 1997 (SE) ................................................. 9703251

(51) Int. Cl.[7] .......................... G01N 33/00; C12Q 1/68; C12P 19/34; C07H 21/02; C07H 21/04
(52) U.S. Cl. ............................ 436/94; 435/6; 435/91.1; 536/23.1; 536/24.3; 536/24.33
(58) Field of Search ........................... 435/6, 91.1, 91.2, 435/183, 283.1, 287.1, 287.2, 288.7; 436/501, 94; 536/23.1, 24.3, 24.33, 25.3, 25.32

(56) References Cited

U.S. PATENT DOCUMENTS 5,646,267 A  7/1997  Stec et al.

FOREIGN PATENT DOCUMENTS

| DE | 3446635 | 6/1985 |
|---|---|---|
| DK | WO 97/05158 | * 2/1997 |
| EP | 0710668 | 5/1996 |
| EP | 0714986 | 6/1996 |
| EP | 0742287 | 11/1996 |
| WO | WO 9211388 | 7/1992 |
| WO | WO 9511912 | 5/1995 |
| WO | WO 9518136 | 7/1995 |
| WO | WO 9705156 | 2/1997 |

OTHER PUBLICATIONS

Weiler et al., Hybridization based DNA screening on peptide nucleic acid (PNA) oligomer arrays. Nucleic Acids Res. 25, 2792–2799, Jul. 1997.*

Cardullo et al., Detection of nucleic acid hybridization by nonradiative fluorescence resonance energy transfer. Proc. Natl. Acad. Sci. USA 85, 8790–8794, 1988.*

* cited by examiner

Primary Examiner—Etha C. Whisenant
Assistant Examiner—Frank Lu
(74) Attorney, Agent, or Firm—Oppedahl & Larson LLP

(57) ABSTRACT

The invention relates to a method for preparing a probe, thus prepared probe, and the use of such a probe for selectively choosing sequence for nucleic acid diagnostic purposes, using preferably homogenous solutions. The invention is based upon a great number of probes having different sequences and lengths which all are complementary to different parts of the nucleic acid to be detected, which probes are synthetised on a solid matrix. The signal which they provide in non-hybridized condition is monitored, whereupon the nucleic acid to be detected is added, and the signal is monitored again. Those probes that show the most significant difference in signal are those, from a sensitivity point of view, that are the most suitable one.

23 Claims, 5 Drawing Sheets

Probe construction

Membrane-PEG-500-GLU-LYS-Capronic acid-PNA-CO-(CH$_2$)$_{10}$—

Thiazole orange (TO)

PNA Sequences

Seq. ID

| | | | | | | | | | | | | | | | | | | | |
|---|---|---|---|---|---|---|---|---|---|---|---|---|---|---|---|---|---|---|---|
| 1 | C | A | G | T | C | T | A | C | T | C | | | | | | | | | |
| 2 | | A | G | T | C | T | A | C | T | C | C | | | | | | | | |
| 3 | | | G | T | C | T | A | C | T | C | C | T | | | | | | | |
| 4 | | | | T | C | T | A | C | T | C | C | T | T | | | | | | |
| 5 | | | | | C | T | A | C | T | C | C | T | T | C | | | | | |
| 6 | | | | | | T | A | C | T | C | C | T | T | C | T | | | | |
| 7 | | | | | | | A | C | T | C | C | T | T | C | T | C | | | |
| 8 | | | | | | | | C | T | C | C | T | T | C | T | C | C | | |
| 9 | | | | | | | | | T | C | C | T | T | C | T | C | C | G | |
| 10 | | | | | | | | | | C | C | T | T | C | T | C | C | G | A |
| 11 | | | | | | | | | | | C | T | T | C | T | C | C | G | A | T |
| 12 | | | | | | | | | | | | T | T | C | T | C | C | G | A | T | A |
| 13 | | | | | | | | | | | | | T | C | T | C | C | G | A | T | A | A |
| 14 | | | | | | | | | | | | | | C | T | C | C | G | A | T | A | A | C |
| 15 | | | | | | | | | | | | | | | T | C | C | G | A | T | A | A | C | A |
| 16 | | | | C | C | T | C | T | T | C | C | T | C | | | | | | |

METHOD FOR THE PREPARATION OF A PROBE FOR NUCLEIC ACID HYBRIDIZATION

DESCRIPTION

1. Technical Field

The present invention relates to a method for the preparation of probes, in particular preparation of selective probes for the identification of nucleic acids; a matrix comprising such probes, and the use of such a probe for the hybridization of nucleic acids.

2. Background of the Invention

Figure 1:
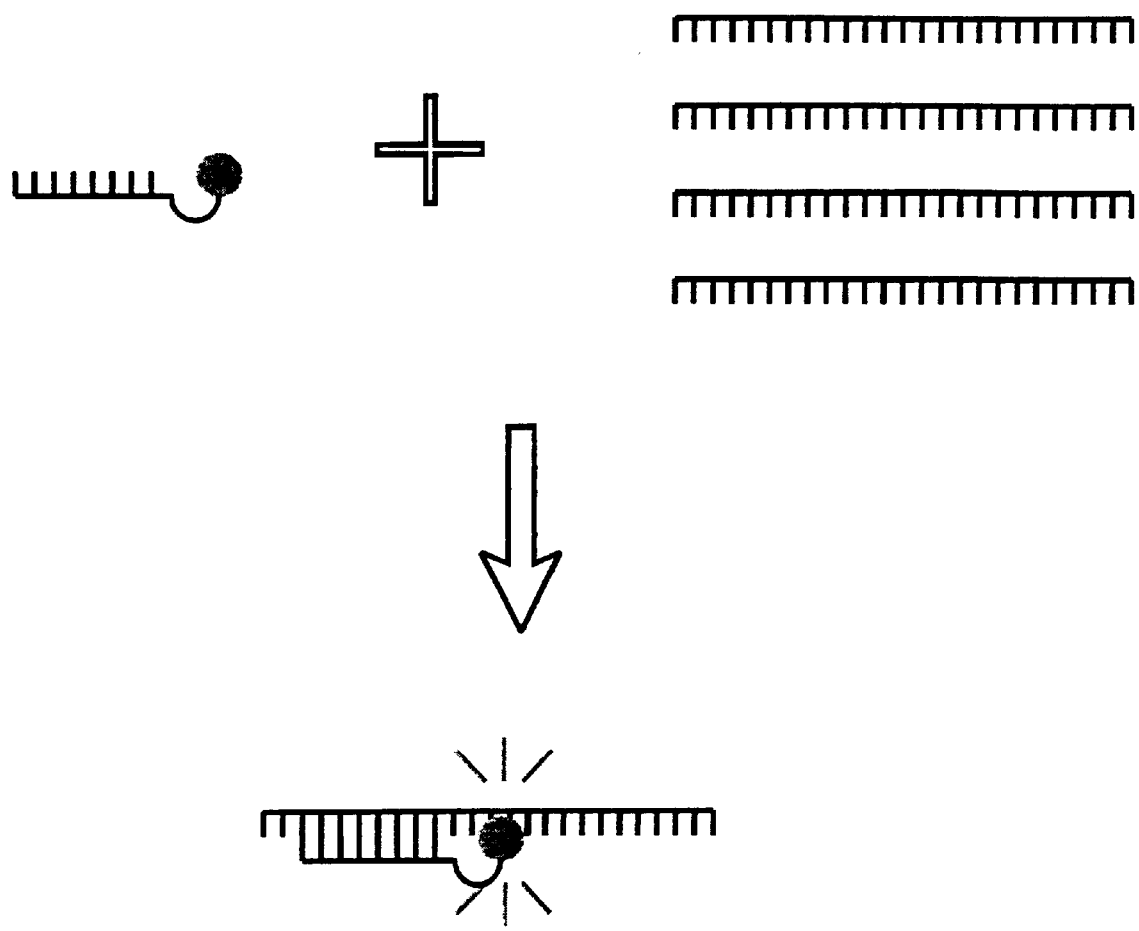

Probes for the hybridization of nucleic acids are used to show the presence of a certain nucleic acid in a test solution. Traditional probes provide no appreciable differences concerning detectable features in free and hybridized conditions but the nucleic acid is determined separation of hybridized and non-hybridized probes (Gillespie & Spiegelman, J. Mol. Biol. 12, 829, 1956). Homogenous test methods, however, use probes the signals of which change at hybridization (FIG. 1). Such probes are composed by a sequence-recognizing part (SID) and a reporting group (RG) (FIG. 2) where SID as a rule is a synthetic oligodeoxy ribonucleic acid (Barton, J., U.S. Pat. No. 5,157,032; Yamana et al., Nucl. & Nucl., 11 (2–4), 383, 1992; Linn et al., EP-A-0 710 668, U.S. Pat. No. 5,597,696) or a nucleic acid analogue (Kubista, PCT/SE97/00953). RG is commonly a colouring agent the fluorescence of which increases at the binding to a nucleic acid. As shown by Nygren et al, *Biopol.*, 46, 39–51 (1998) the properties of such colouring agents are heavily dependent on the sequence of the nucleic acid. This, as shown in PCT/SE97/00953, leads to the fact that both the background fluorescence of free probes as well as the fluorescence of the hybridized probes depend on the sequence of the SID and consequently of the target sequence (MS) selected being complementary to SID. Further, it is probable. that even the sequence closest to MS is of importance.

Nucleic acids can, as a rule, be determined selectively using a great number of probes which differ in the SID part by recognizing different MS which constitute unique segments of the nucleic acid. A nucleic acid having the length m, comprises m+n+1 stretches of the length n which all are potential MS. As the length of MS has not to be particularly long in order to be unique (a 15 bases long stretch appears as an average once per $4^{15}=10^9$ bases) a great number of probes can be directed to a certain nucleic acid. A genome having 1000 bases, which is rather characteristic of a virus can be determined using 981 probes having the length of 20 bases, 982 of the length 19, 983 of the length 18, etc. Bacterial genomes which 5 are considerably larger, can be determined using a still greater number of different probes. In order to determine a specific mutation the choice is more restricted as the sequence of the probe has to overlap the presumptive mutation, but still there are several alternatives.

In PCT/SE97/00953 one selects the sequence of SID starting from the knowledge of the known properties of RG, and for asymmetric cyanine dye stuffs SID's are proposed the terminal bases, preferably, mixed pyrimidines (-TT or -CT). This strategy comprises several restrictions. On one hand detailed studies of the properties of the dye stuff are required which can not be trivially extrapolated to the properties of the probes, due to differences in experimental conditions, etc, and on the other hand the sequence requirements as a rule of an indefinite number of sequences (⅛ of all sequences, e.g., end with either -TT or -CT). Finally, there is no consideration concerning the sequence closest to MS.

The present invention solves these problems. Basically, it is a method for determining which of a great number of potential probes to a certain nucleic acid, that has the lowest background signal and which of these that obtains the strongest signal at hybridization. The difference in determinations is the increase in signal strength which is obtained using the different probes.

Description of FIGS.

FIG. 1. Principle for homogenous testing

Figure 2:
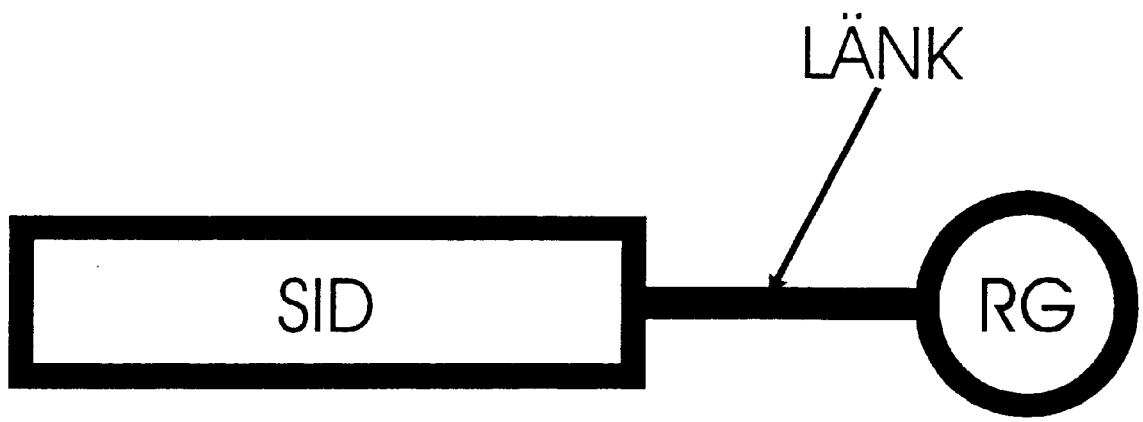

FIG. 2. Probe for homogenous testing comprising a sequence recognizing part (SID) and a reporting group (RG)

FIGS. 3A–C. Principle showing how the most suitable probe for a nucleic acid from a sensitivity aspect can be identified.

A: Examples of probes which all recognize the same nucleic acid

B: These probes being synthetised onto a solid matrix

C: The fluorescence of probes monitored in free as well as hybridized conditions, those providing the greatest increase in signal strength being the most suitable ones.

Figure 4:
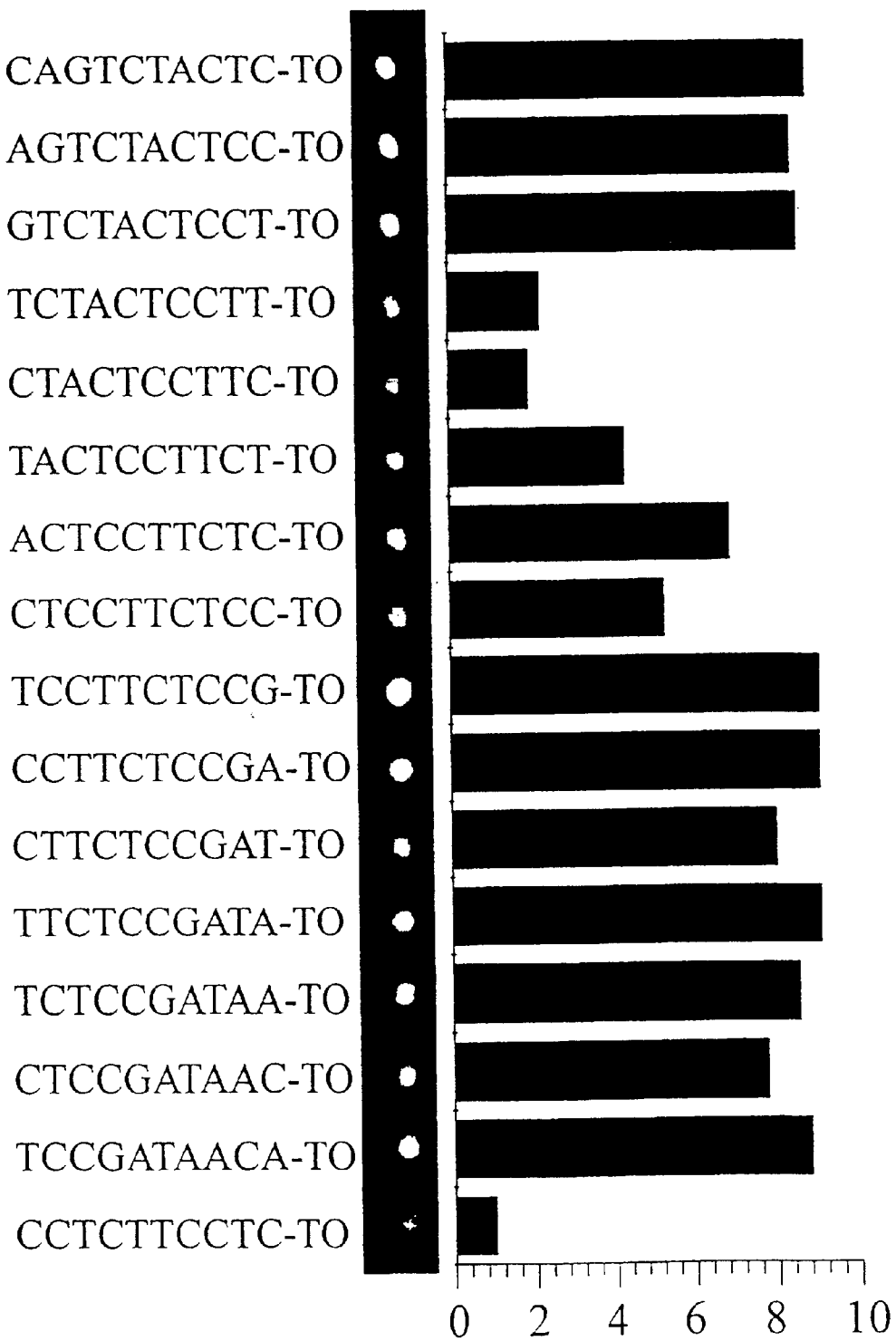
Figures 5, 5B:
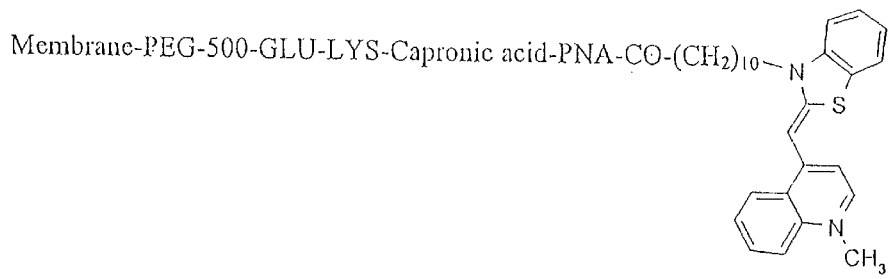

FIG. 4 shows different probes and their different fluorescence intensities prior to. hybridization FIGS. 5A and 5B illustrate a construction of a probe designed in an embodying example with a sequence modification of the different probes the intensities of which are shown in FIG. 4.

Description of the invention

Deoxyribonucleic acids and several nucleic acid analogues, such as peptide nucleic acids (PNA) are generally synthetised using a solid phase synthesis which i.a., allows the synthesis of a great number of fragments having different sequences and different lengths, as well, on a matrix (Khrapko et al., FEBS Lett. 256, 118. 1989; Southern, E., et al., Genomics 13, 1008, 1992; Caviani-Pease, et al., Proc. Natl. Acad. Sci., 91, 5022, 1994; Weiler et al., *Nucl. Acids Res.* 25, 2792, 1997). The fragments on this matrix can be hybridized using a labelled nucleic acid, e.g., fluorescent or radioactive groups, and the degree of hybridization can be determined from the signal of the nucleic acid. This technology has several applications and is often called DNA-chip technology.

Figure 3:
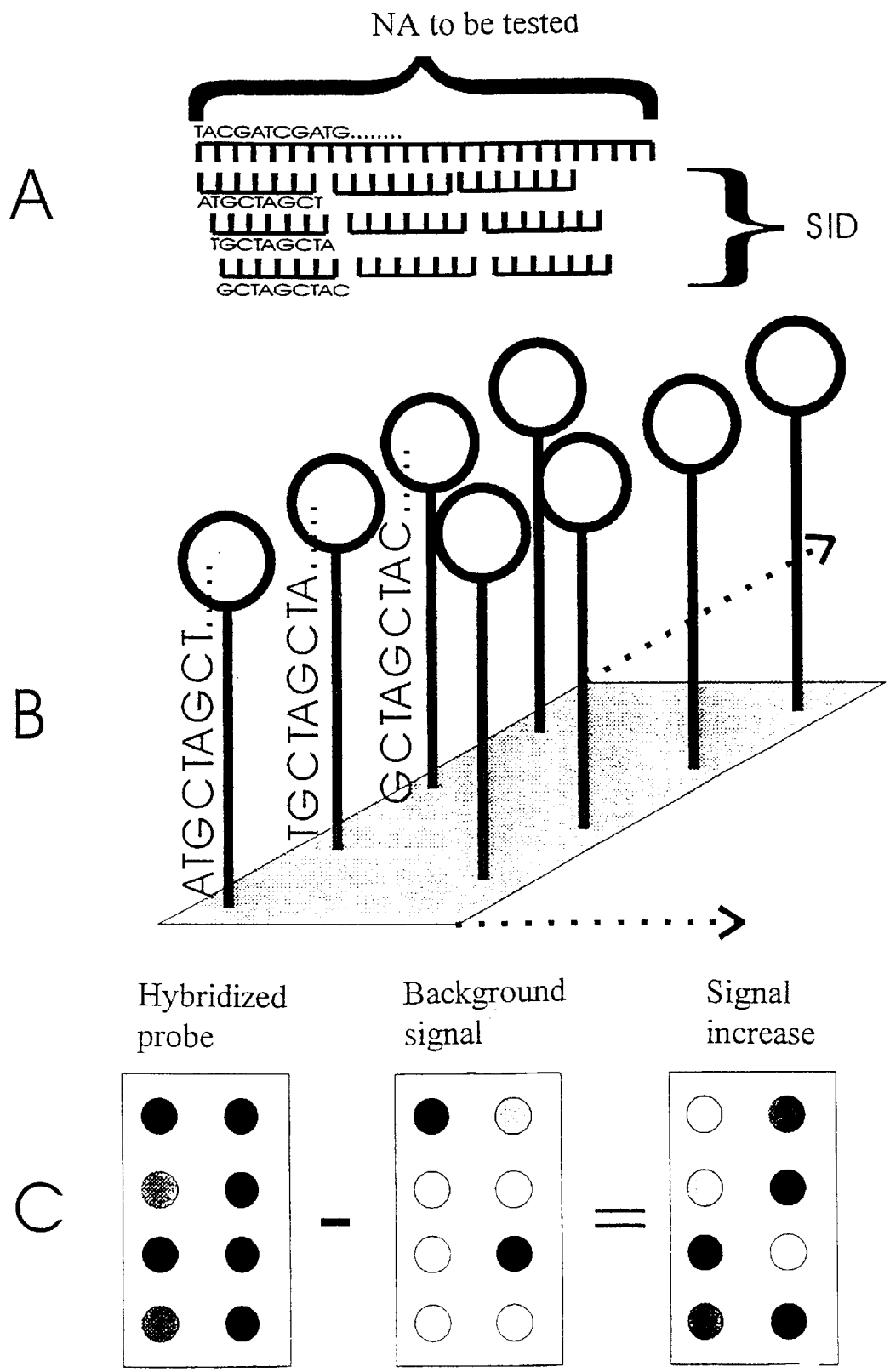

In the present invention the DNA-chip technology is utilized in order to determine which of a great number of probes, which all, having a specificity enough, recognizes a certain nucleic acid suitable for nucleic acid hybridization, and then preferably in a homogenous solution. Probes, i.e., oligodeoxyribonucleic acids or nucleic acid analogues provided with reporting groups (RG) which all being complementary enough and specific enough to a certain nucleic acid are synthetised on a matrix (FIG. 3). The signal, preferably fluorescence, which they give raise to, i.e., the background signal is monitored. Then a certain nucleic acid is added and the fluorescence, this time from the hybridized probes, are registered. The difference in signal strength at these determinations is the increase of signal strength obtained by the different probes. Those which show the greatest difference in signal strength are those from a sensitivity point of view being the most suitable ones.

Different matrix materials can be used, such as cellulose substrates, metal substrates and polymer substrates. When using metal substrates the metal is most often provided with a coating of an amino acid to facilitate adherence. When using cellulose substrates a first nucleotide is attached to the substrate whereupon further nucleotides are synthetised onto the first one being attached until one has obtained a suitable nucleotide sequence.

The present probes can be used for the analysis of nucleic acid/s in the form of mRNA, DNA, PNA, PNA-PNA complexes, or DNA-PNA complexes.

The difference in signal strength at the hybridization can be obtained as a result of changing properties of the probes, i.e., a, signal difference non-hybridized condition vis-a-vis hybridized condition, or one hybridizes to a labelled nucleic acid using another reporting group, RG', whereby the difference in signal strength is obtained when the RG-group of the probe and the RG'-group of the target DNA approach each other. RG and RG' can the same or different. In a system comprising pyrene the fluorescence properties markedly when two pyrenes are brought into contact with each other, whereby an eximer fluorescence is obtained. Example of two different RG, RG' are energy transfer pairs such as fluorescein/tetramethyl rhodamine or fluorophore/quencher pair.

The invention will be described below with reference to an example illustrating the invention, without, however, being restricted thereto.

EXAMPLE

Fifteen 10-bases long PNA-thiazole orange probes, complementary to different segments of the sequence GTCAGATGAGGAAGAGGCTATTGT, Seq. ID NO: 18 and a probe being complementary in a parallel orientation to the central polypurine region, were synthetised onto a Perspective-PP-NH$_2$-membrane (separated from the membrane with PEG-500-Glu-Lys-capronic acid linker) using an ABIMED ASP 222 Automated SPOT Robot (Weiler, J. et al., *Nucleic Acids Res.*, 25, 2792, (1997), FIG. 1). The PNA monomers were attached as described by Weiler et al, supra. In the last step the thiazole orange dye stuff substituted with a carboxylic acid alkyl linker was activated and reacted in the same way as the Fmoc-PNA-monomers. After synthesis the side chain protecting groups were eliminated from the PNA oligomers by treatment using 90% TFA/5% of water/5% triethyl silane for 1 hr (TFA=trifluoro acetic acid).

The membrane was then moistened in a 10 mM borate buffer at pH 8.5 comprising an addition of 100 mM NaCl for 2 hrs, and was lightened using a standard UV-lamp having $\lambda_{max}$=312 nm; and was photographed using a CCD camera (FIG. 4). The background fluorescence of the probes have been expressed in relation to probe 16 (CCTCTTCCTC-TO) Seq. ID No: 16, which exhibits the weakest intensity prior to hybridization and which, thereby, is expected to provide the greatest difference in signal strength after hybridization.

What is claimed is:

1. A method for preparing a hybridization probe for use in a hybridization assay with a target nucleic acid, (a) obtaining a test matrix comprising a plurality of species of oligodeoxyribonucleic acids or nucleic acid analog probes which each comprise a sequence recognizing portion (SID) and a reporting group portion (RG), and a matrix support, wherein said oligodeoxyribonucleic acids or nucleic acid analogues are fixedly attached to the matrix support at defined locations and are sufficiently complementary to different portions of the target nucleic acid to permit hybridization therewith, and wherein the RG portions of the probes are selected to produce a first detectable signal when unhybridized to a nucleic acid and a second detectable signal distinguishable from the first detectable signal when hybridized to a nucleic acid;

(b) determining a background signal corresponding to the first detectable signal for each defined location;

(c) contacting the test matrix with a sample of the target nucleic acid and then detecting a subsequent signal from each defined location, said subsequent signal being the second detectable signal if hybridization has occurred and the first detectable signal if hybridization has not occurred;

(d) comparing the first signal to the subsequent signal;

(e) rating the hybridization probes at each defined location in order of the difference between the first signal and the subsequent signal, wherein higher ratings are assigned to hybridization probes for which the difference between the first signal and the subsequent signal are larger; and (f) selecting a probe with a high rating relative to other probes tested and preparing copies of this selected probe for use in hybridization assays.

2. The method of claim 1, wherein the SID is a peptide nucleic acid (PNA) or a peptide nucleic acid (PNA)-derivative.

3. The method of claim 1, wherein the first signal and the second signal differ in signal strength.

4. The method according to claim 1, wherein the target nucleic acid is labelled with a second reporter group RG' which may be the same as or different from the first reporter group, and wherein RG and RG' interact when the target nucleic acid hybridizes with the test matrix to produce a second detectable signal of different signal strength than the first detectable signal.

5. The method according to claim 1, wherein the matrix support comprises a material selected from among cellulose substrates, metal substrates, polymer substrates and combinations thereof.

6. The method according to claim 1, wherein the probes are attached to the matrix support by means of adsorption.

7. The method according to claim 1, wherein the first and second detectable signals are fluorescent signals.

8. The method according to claim 1, wherein the SID is a deoxyribonucleic acid, a deoxyribonucleic acid derivative or a deoxyribonucleic acid analog.

9. The method according to claim 1, wherein the test matrix comprises at least ten species of probes.

10. The method according to claim 9, wherein the first signal and the second signal differ in signal strength.

11. The method according to claim 9, wherein the target nucleic acid is labelled with a second reporter group RG' which may be the same as or different from the first reporter group, and wherein RG and RG' interact when the target nucleic acid hybridizes with the test matrix to produce a second detectable signal of different signal strength than the first detectable signal.

12. The method according to claim 1, wherein the test matrix comprises at least 100 species of probes.

13. The method according to claim 1, wherein the test matrix comprises at least 1000 species of probes.

14. A matrix for evaluating nucleic acid hybridization probes, comprising a plurality of species of probes comprising oligodeoxyribonucleic acids or nucleic acid analogs, each of said species of probe comprising a sequence recognizing portion (SID) and a reporting group portion (RG), and a matrix support, wherein said probes are fixedly attached to the matrix support and are sufficiently complementary to different parts of a target nucleic acid to permit hybridization therewith, and wherein the RG portions of the probes are selected to produce a first detectable signal when unhybridized to a nucleic acid and a second detectable signal distinguishable from the first detectable signal when hybridized to a nucleic acid.

15. The matrix according the claim 14, wherein the SID is a peptide nucleic acid (PNA) or a peptide nucleic acid (PNA)-derivative.

16. The matrix of claim 14, wherein the first signal and the second signal differ in signal strength.

17. The matrix according to claim 14, wherein the matrix support comprises a material selected from among cellulose substrates, metal substrates, polymer substrates and combinations thereof.

18. The matrix according to claim 14, wherein the probes are attached to the matrix support by means of adsorption.

19. The matrix according to claim 14, wherein the first and second detectable signals are fluorescent signals.

20. The matrix according to claim 14, wherein the SID is a deoxyribonucleic acid, a deoxyribonucleic acid derivative or a deoxyribonucleic acid analog.

21. The matrix according to claim 14, wherein the test matrix comprises at least ten species of probes.

22. The matrix according to claim 14, wherein the test matrix comprises at least 100 species of probes.

23. The matrix according to claim 14, wherein the test matrix comprises at least 1,000 species of probes.

* * * * *

SEQUENCE LISTING

<160> NUMBER OF SEQ ID NOS: 18

<210> SEQ ID NO 1
<211> LENGTH: 10
<212> TYPE: DNA
<213> ORGANISM: synthetic construct

<400> SEQUENCE: 1
cagtctactc                                                          10

<210> SEQ ID NO 2
<211> LENGTH: 10
<212> TYPE: DNA
<213> ORGANISM: synthetic construct

<400> SEQUENCE: 2
agtctactcc                                                          10

<210> SEQ ID NO 3
<211> LENGTH: 10
<212> TYPE: DNA
<213> ORGANISM: synthetic construct

<400> SEQUENCE: 3
gtctactcct                                                          10

<210> SEQ ID NO 4
<211> LENGTH: 10
<212> TYPE: DNA
<213> ORGANISM: synthetic construct

<400> SEQUENCE: 4
tctactcctt                                                          10

<210> SEQ ID NO 5
<211> LENGTH: 10
<212> TYPE: DNA
<213> ORGANISM: synthetic construct

<400> SEQUENCE: 5
ctactccttc                                                              10

<210> SEQ ID NO 6
<211> LENGTH: 10
<212> TYPE: DNA
<213> ORGANISM: synthetic construct

<400> SEQUENCE: 6
tactccttct                                                              10

<210> SEQ ID NO 7
<211> LENGTH: 10
<212> TYPE: DNA
<213> ORGANISM: synthetic construct

<400> SEQUENCE: 7
actccttctc                                                              10

<210> SEQ ID NO 8
<211> LENGTH: 10
<212> TYPE: DNA
<213> ORGANISM: synthetic construct

<400> SEQUENCE: 8
ctccttctcc                                                              10

<210> SEQ ID NO 9
<211> LENGTH: 10
<212> TYPE: DNA
<213> ORGANISM: synthetic construct

<400> SEQUENCE: 9
tccttctccg                                                              10

<210> SEQ ID NO 10
<211> LENGTH: 10
<212> TYPE: DNA
<213> ORGANISM: synthetic construct

<400> SEQUENCE: 10
ccttctccga                                                              10

<210> SEQ ID NO 11
<211> LENGTH: 10
<212> TYPE: DNA
<213> ORGANISM: synthetic construct

<400> SEQUENCE: 11
cttctccgat                                                              10

<210> SEQ ID NO 12
<211> LENGTH: 10
<212> TYPE: DNA
<213> ORGANISM: synthetic construct

<400> SEQUENCE: 12

-continued

```
ttctccgata                                                          10

<210> SEQ ID NO 13
<211> LENGTH: 10
<212> TYPE: DNA
<213> ORGANISM: synthetic construct

<400> SEQUENCE: 13
tctccgataa                                                          10

<210> SEQ ID NO 14
<211> LENGTH: 12
<212> TYPE: DNA
<213> ORGANISM: synthetic construct

<400> SEQUENCE: 14
ctccgatata ac                                                       12

<210> SEQ ID NO 15
<211> LENGTH: 10
<212> TYPE: DNA
<213> ORGANISM: synthetic construct

<400> SEQUENCE: 15
tccgataaca                                                          10

<210> SEQ ID NO 16
<211> LENGTH: 10
<212> TYPE: DNA
<213> ORGANISM: synthetic construct

<400> SEQUENCE: 16
cctcttcctc                                                          10

<210> SEQ ID NO 17
<211> LENGTH: 11
<212> TYPE: DNA
<213> ORGANISM: synthetic construct

<400> SEQUENCE: 17
tacgatcgat g                                                        11

<210> SEQ ID NO 18
<211> LENGTH: 24
<212> TYPE: DNA
<213> ORGANISM: synthetic construct

<400> SEQUENCE: 18
gtcagatgag gaagaggcta ttgt                                          24
```